(12) United States Patent
Elder

(10) Patent No.: US 11,877,890 B2
(45) Date of Patent: Jan. 23, 2024

(54) DEVICE AND METHOD FOR SECURING A TRANSDUCER IN POSITION

(71) Applicant: Cassandra Elder, Raleigh, NC (US)

(72) Inventor: Cassandra Elder, Raleigh, NC (US)

( * ) Notice: Subject to any disclaimer, the term of this patent is extended or adjusted under 35 U.S.C. 154(b) by 108 days.

(21) Appl. No.: 16/771,165

(22) PCT Filed: Dec. 12, 2018

(86) PCT No.: PCT/US2018/065137
§ 371 (c)(1),
(2) Date: Jun. 9, 2020

(87) PCT Pub. No.: WO2019/118564
PCT Pub. Date: Jun. 20, 2019

(65) Prior Publication Data
US 2021/0186459 A1 Jun. 24, 2021

Related U.S. Application Data

(60) Provisional application No. 62/597,472, filed on Dec. 12, 2017.

(51) Int. Cl.
*A61B 8/00* (2006.01)
*A61B 5/00* (2006.01)
*A61B 8/02* (2006.01)
*A61B 8/08* (2006.01)

(52) U.S. Cl.
CPC .......... *A61B 8/4209* (2013.01); *A61B 5/6832* (2013.01); *A61B 8/02* (2013.01); *A61B 8/0866* (2013.01)

(58) Field of Classification Search
CPC .. A61B 5/02411; A61B 5/6831; A61B 8/4227
See application file for complete search history.

(56) References Cited

U.S. PATENT DOCUMENTS 7,789,836 B2 * 9/2010 Van Wyk ............. A61B 8/4227
600/459
2009/0005690 A1 * 1/2009 Irland ................... A61B 8/4281
600/472

(Continued)

FOREIGN PATENT DOCUMENTS

EP 3466329 A1 * 4/2019 ......... A61B 5/02411

*Primary Examiner* — Bill Thomson
*Assistant Examiner* — Aminah Asghar
(74) *Attorney, Agent, or Firm* — Kathleen M. Lynch

(57) ABSTRACT

An assembly and method for positioning a fetal heart transducer against skin. The assembly includes a strip having first and second ends and openings along its length, first and second fixation devices, each device having first and second surfaces, the first surface having adhesive thereon. A protuberance extends outwardly from the second surface. The assembly includes a fetal heart transducer. The first fixation device is secured to the skin at a first location and the protuberance of the first fixation device is received into a first opening on the first end of the strip. The first surface of the second fixation device is secured to the skin at a second location and the protuberance of the second fixation device is received into a second opening on the second end of the strip. The fetal heart transducer is secured between first and second fixation devices and beneath the strip.

10 Claims, 13 Drawing Sheets

(56) References Cited

U.S. PATENT DOCUMENTS

| | | | | |
|---|---|---|---|---|
| 2010/0274099 A1* | 10/2010 | Telfort | ............... | A61B 7/003 |
| | | | | 600/300 |
| 2011/0282178 A1* | 11/2011 | Andersen | ............ | A61B 5/4362 |
| | | | | 600/588 |
| 2017/0188947 A1* | 7/2017 | Connor | ............... | A61B 5/369 |

* cited by examiner

DEVICE AND METHOD FOR SECURING A TRANSDUCER IN POSITION

PRIORITY

This application is a National Stage Entry of International Application No. PCT/US2018/065137, filed Dec. 12, 2018, which claims benefit from U.S provisional patent application serial no. 62/597,472 filed Dec. 12, 2017, the contents of which is incorporated in its entirety.

FIELD

The embodiments herein describe a device and method for positioning a fetal heart transducer securely against the skin of an expectant mother.

BACKGROUND

Modern medical technology enables the child birth process to be more controlled than ever before. With the development of ultrasonic technology, medical personnel can monitor a fetal heart rate (FHR) during a substantial part of the fetal life through delivery.

The FHR is measured using ultrasonic technology. A transducer is placed on the skin of an expectant mother. The sound waves from the pumping of the fetal heart are received by the transducer and communicated to the receiver for measurement and monitoring. In order to obtain accurate and complete FHR data, the transducer must maintain contact with the skin of the patient.

The fetal heart rate (FHR) is an important measure during the labor and delivery process. The loss of the FHR can cause anxiety for patients and their families, as well as concern for medical personnel. The loss of a FHR can result from the change in fetal position, the lack of contact between the fetal heart transducer and the patient's skin, or fetal distress including cardiac arrest and death. In order to intervene at the earliest sign of fetal distress, the FHR must be accurate and continuously monitored.

For continuous monitoring of the FHR in labor and delivery, expectant mothers are usually fitted with one or more belts worn around the torso that serve to support and hold one or more fetal heart transducers (FHT) in position. However the belts have proven to be ineffective at maintaining the fetal heart transducer position. The belts tend to move as the patient shifts position in bed. When that occurs, medical personnel is required to further adjust the FHT and re-secure it to or under the belt.

In addition, many expectant mothers receive an epidural during labor. As such, the belts often interfere with the epidural dressing and/or catheter itself. This can result in a dislodgement of the epidural which can result in a loss of pain medication to the mother. In addition, the belt movement in an around the epidural site can cause discomfort and/or further injury to the mother, particularly during labor.

Another issue relating to the FHT belt is that the belts become contaminated with blood or bodily fluids during the labor process. When this occurs, the entire belt must be changed and the FHT repositioned. The change of belts is costly in both materials and time.

Often times the loss of the FHR is due to the movement of the transducer caused by the movement of a support belt and/or patient movement. Movement by a patient, especially one experiencing labor pains, is expected. As a result, medical personnel, particularly labor and delivery nurses, are needed to reposition the FHT and re-secure it to the belt when there is a loss of FHR due to the mother's movement. In addition, because the belt is keeping the FHT in position, it limits a patient's movement which can be particularly uncomfortable for a mother in labor.

In addition, obese patients require additional care in obtaining and maintaining the FHR. The FHR is more difficult to detect in an obese patient due to the increased amount of fatty tissue surrounding the womb. Typically a labor and delivery nurse needs to spend additional time with an obese patient to first find the FHR and then to position the transducer at the location to obtain a continuous FHR reading. This process often takes more time because of the weaker signal. Loss of FHR signal also occurs in mothers with extremely contoured bellies. The significant contours make it a challenge to maintain contact between the FHT and the mother's skin. The existing belt system is often ineffective because the belt does not easily lie and hold the FHT effectively against the skin.

The FHR signal may also be lost during the final stages of labor. As the fetus travels down the birth canal, it places its heart at a further distance from the present FHT systems. As such, the systems are often challenged to track and maintain the FHR during these final birthing stages. In addition, because the FHR signal can be weak and difficult to track, the FHR is sometimes confused with the maternal heart rate. This can be a fatal error and create a false sense of security, especially when the fetus is in distress.

The monitoring of the FHR also occurs with bedridden expectant mothers. In these cases, the FHT is used to continuously monitor the FHR for a patient who has been hospitalized due to complications associated with her pregnancy. This includes premature delivery, fetal development issues and the like.

Some belts do not encircle the patient's torso but are one length and have two adhesive areas for securing the device to the patient. These systems do not provide for easy readjustment as the entire assembly must be removed and reapplied or replaced. In addition, the length between the two adhesive areas may lose its tension against the FHT. When this occurs, the entire assembly will need to be readjusted or replaced.

The existing belts and systems used to position the FHT do not provide the necessary freedom of movement needed by the patient to be comfortable and manage the labor contractions. In addition, the existing belts are often destroyed due to contamination during the labor process. This results in additional costs in time and money to the hospitals. Finally, the belts interfere with the epidural site and remove the epidural catheter due to patient movement. For these reasons, a better solution is needed to accurately position the FHT on the mother's skin but provide freedom of movement and no interference with other medical equipment.

Thus there is a need for an assembly for securely positioning a FHT against the skin of an expectant mother so that the assembly can be adjusted and re-adjusted without the need to remove, reapply or replace the entire assembly. In addition, there is a need for an assembly for securely positioning a FHT against the skin of an expectant mother that does not interfere with existing medical equipment. There is yet a further need for an assembly for securely positioning a FHT against the skin of an expectant mother that enables the mother to move freely with the confidence that the FHT is maintaining contact with her skin and providing continuous and accurate FHR readings.

DETAILED DESCRIPTION OF THE DRAWINGS

DETAILED DESCRIPTION OF THE EMBODIMENTS

Figure 1:
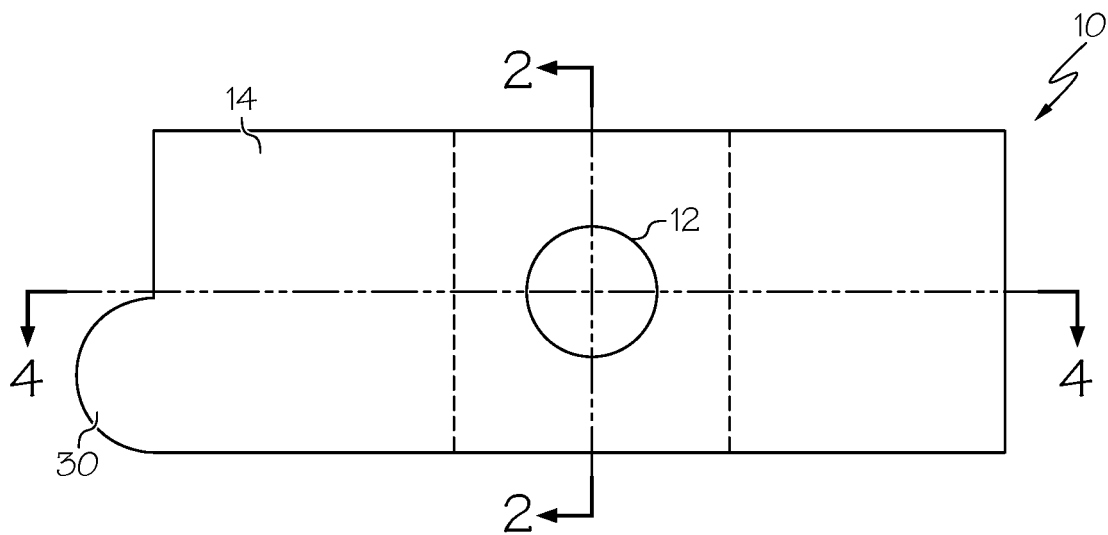
FIG. 1 is a top view of a first embodiment described herein.
Figure 2:
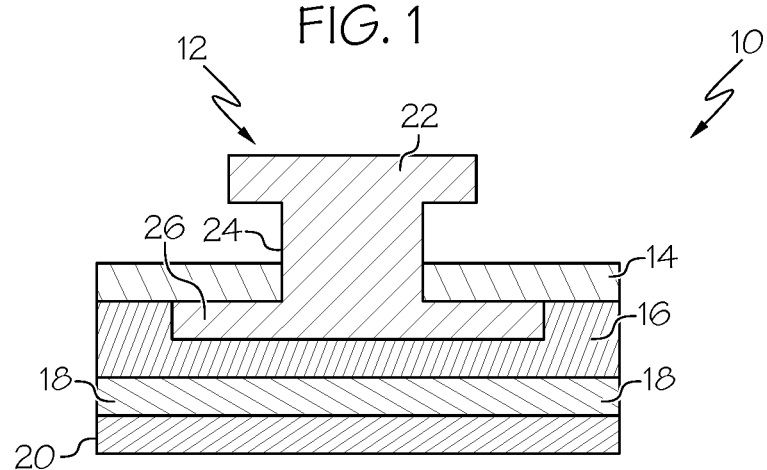
FIG. 2 is a side sectional view of the embodiment of FIG. 1 taken along line 2-2.
Figure 3:
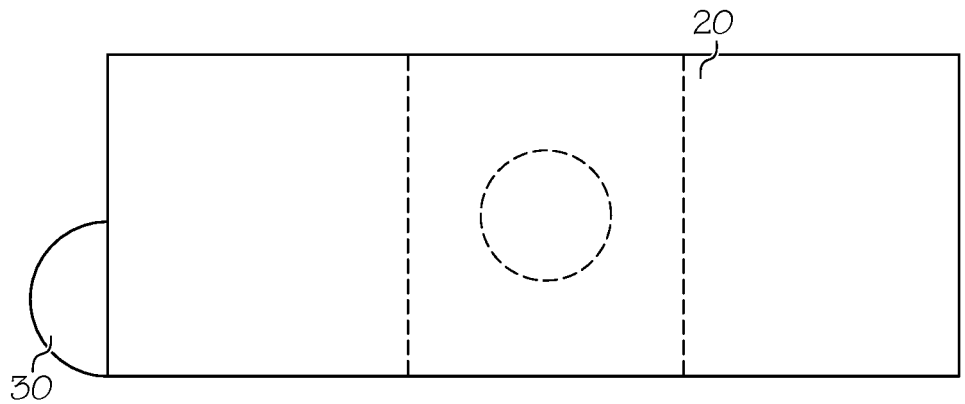
FIG. 3 is a bottom view of the embodiment of FIG. 1.
Figure 4:
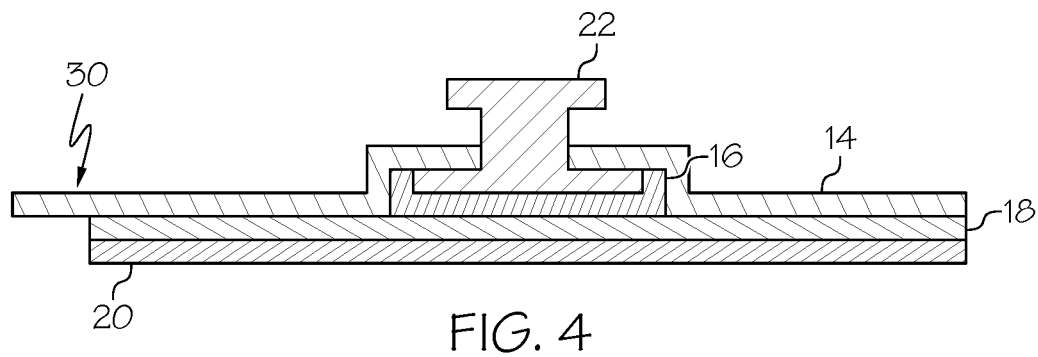
FIG. 4 is a front sectional view along lines 4-4 of the embodiment of FIG. 1.

The embodiments described herein are devices and systems for use with a medical transducer, and in particular, a fetal heart rate (FHR) transducer. The first embodiment 10 is directed to a device for securing the position of a medical transducer and is shown in FIGS. 1-6. Turning first to FIG. 2, the first embodiment 10 is shown in cross-section. The first embodiment 10 includes a button assembly 12. The button assembly 12 includes a fabric layer 14, cushioning layer 16, an adhesive layer 18 and a liner 20 for the adhesive layer.

The fabric layer 14 of the first embodiment is preferably made of medical grade fabric. The fabric layer 14 is adhered to a cushioning layer 16. The fabric and cushioning layers may be adhered by means of a chemical adhesive or by thermal adhesion. The cushioning layer 16 is preferably made of a medical grade foam having certain characteristics relating to compressibility, strength, and the like. The adhesive layer 18 is applied to the entire lower surface of the cushioning layer and the lower surface of the button assembly which will be described in more detail below. The liner 20 is applied to the lower surface of the adhesive layer 18 to protect it prior to use. Preferably, the liner 20 has a tab 30 extending beyond the perimeter of the fabric 14 and cushioning 16 layers. The tab 30 is designed to be easily grasped by the user to quickly remove the liner 20 and apply the first embodiment device 11 to a patient.

The button assembly 12 further includes a button 22, a central stem 24, and a button base 26. The button assembly 12 extends through the upper surface of the fabric layer 14 and is adjacent to the cushioning layer 16. Both the button 22 and button base 26 are substantially planar. The button base 26 is sized to be slightly larger in size than the button 22 to help stabilize the button assembly 12 during use, which will be discussed in more detail below. The stem 24 extends perpendicular between the button 22 and the button base 26. The button 22 is sized and shaped to be received into a slot of a length of adjustable strapping having incremental slits along the length of the strapping, which will be described in more detail below.

Figure 5:
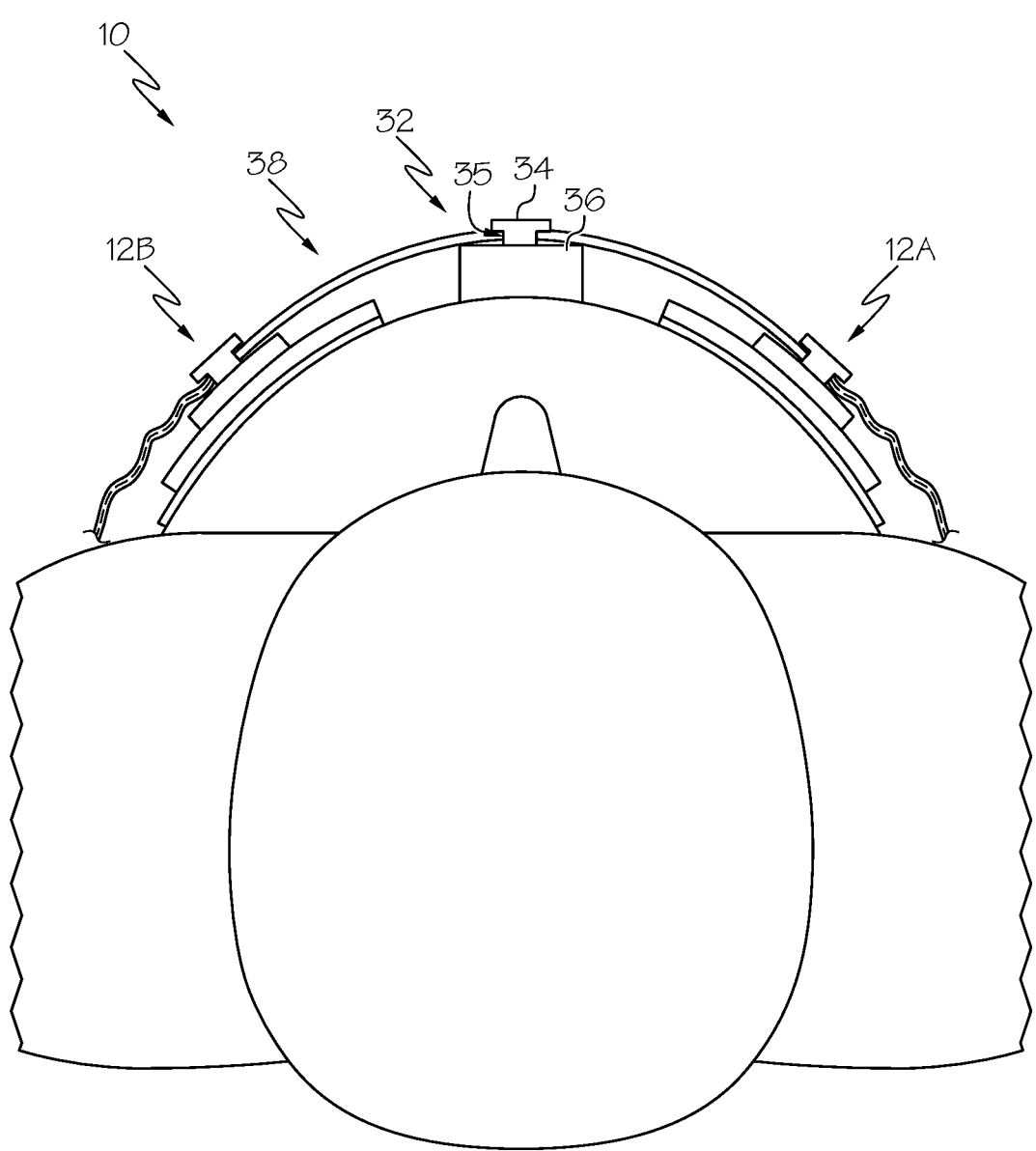
FIG. 5 is a front view of the embodiment of FIG. 1 in use.
Figure 6:
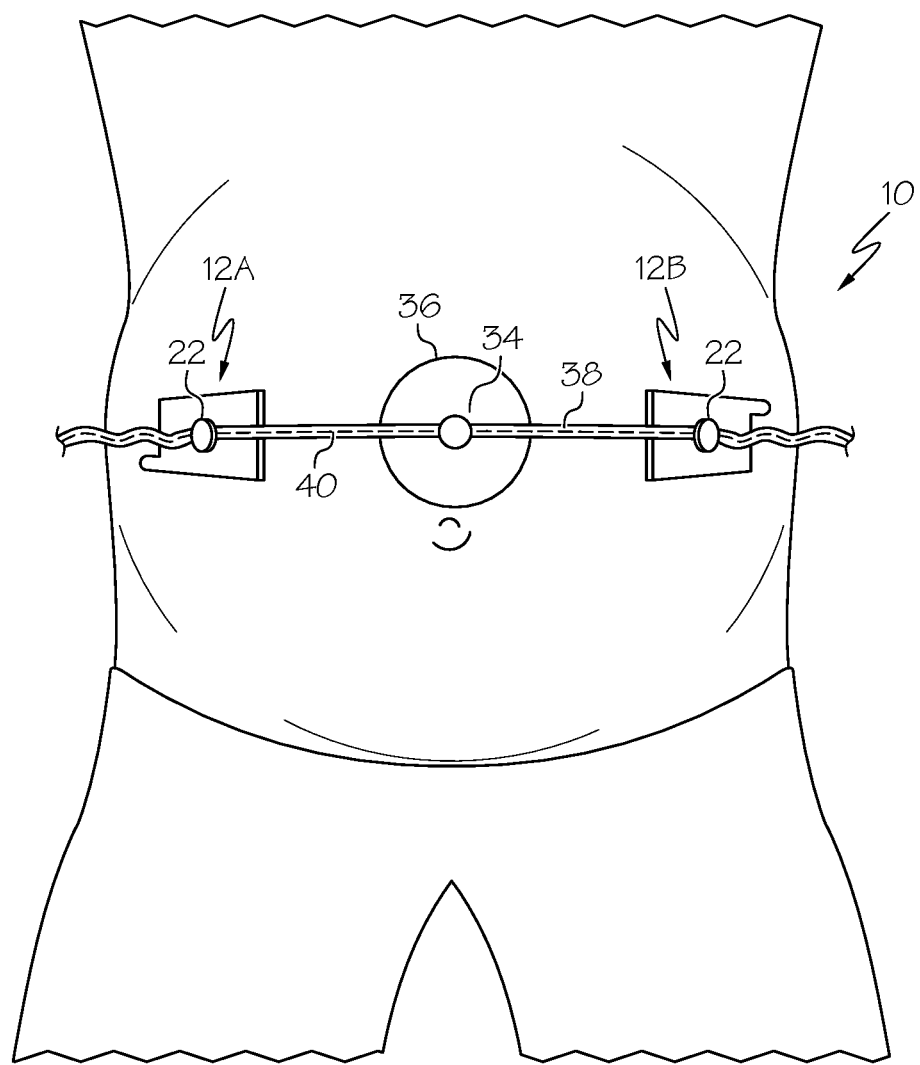
FIG. 6 is a top view of the embodiment shown in FIG. 5.

The first embodiment 10 is designed to be positioned on either side of a medical transducer 32, such as a fetal heart rate transducer, shown in its installed position in FIGS. 5 and 6. As shown in FIG. 5, the fetal heart rate transducers 32 typically have a knob 34 extending from the top of the housing 36 for use in either grasping the transducer or for positioning the transducer. The knob 34 is fixed to the housing by means of a knob stem 35. The medical transducer 32 is typically positioned between the two devices of the first embodiment 10 using medical grade strapping 38 having incremental slits 40 along the length thereof.

In use, a qualified medical person manually maneuvers the medical transducer 32 over the expectant mother's abdomen to find the FHR. This can be challenging because of the mother's size, (sound waves do not travel well through significant layers of fat), and/or the position of the fetus. Often the fetus can move within the womb to avoid being near a transducer. Once a signal is found that is clear and steady, the position of the transducer 32 can be fixed. This is accomplished by first fixing the devices button assemblies 12 in place to support the position of the transducer 32 which will be described below.

The position at which the first button assembly (referred herein as "12A" for explanatory purposes) is placed is dependent upon the desired position of the transducer 32. If the desired transducer 32 position is atop a mother's protruding belly, then the likely position of the first button assembly 12A would be on one side of the protruding belly. If the desired position of the transducer 32 is on the underside of a mother's protruding belly, then the position of the first button assembly 12A may be on one side of the underside area of the belly and slightly above the transducer 32 position so as to provide some uplifting support and to use the protrusion of the belly to provide further tension. The position of the transducer 32 will differ with each patient and fetus and may change over time if the fetus or patient moves.

Returning to positioning the first button assembly 12A, this is achieved by grasping the tab 30 and removing the liner 20 that protects the adhesive layer 18. Then the user, places the first button assembly 12A on the skin of the patient at the desired location. Looking at FIGS. 5 & 6, that position is to the right of center on the mother's belly. The adhesive 18 sticks to the skin and enables the button assembly 12A to remain fixed in that position.

After the first button assembly 12A is positioned, the position of the second button assembly 12B is determined. Typically, the position of the second button assembly 12B would be on the opposite side of the first button assembly 12A from the FHR transducer 32. The second button assembly 12B is attached to the patient's skin as described above by removing the liner 20 and placing it on the skin of the patient. Looking at FIGS. 5 & 6, that position is to the left of center on the mother's belly.

A length of strapping 38 is cut to accommodate the length between the two devices 12A, B. A slit 40 midway along the length of the strapping 38 is received into the knob 34 of the transducer 32. Subsequently, a slit 40 at one end of the strapping 38 is received into the button 22 of the first button assembly 12A. A slit 40 at the opposing end of the strapping 38 is received into the button 22 of the second button assembly 12B. The slits 40 received into the buttons 22 of the devices 11 and into the knob 34 of the transducer 32 may all be moved and new slits received into the respective buttons to adjust the tension of the strapping 38 to provide greater support to the transducer and ensure that its position is secure.

The tension in the strapping 38 between the transducer 32 and the first and second button assemblies 12A, B maintains a pressure on the transducer that enables the transducer to remain fixed in the desired position. This frees up medical personnel to attend to other matters secure in the knowledge that the transducer 32 is in a secure position and is providing continuous fetal vital signs to the monitor [not shown]. This also provides the expectant mother with some level of freedom in that she is able to move about her bed and change positions without fear of losing the signal from the transducer 32. So long as the signal remains strong, the transducer 32, fixed in position, will be able to communicate the signal to the monitor. The continual readings from the transducer 32 provide medical personnel with continually updated fetal data. This provides both medical personnel and the mother with a sense of confidence that the fetal health and well being is being continuously monitored.

Figure 7:
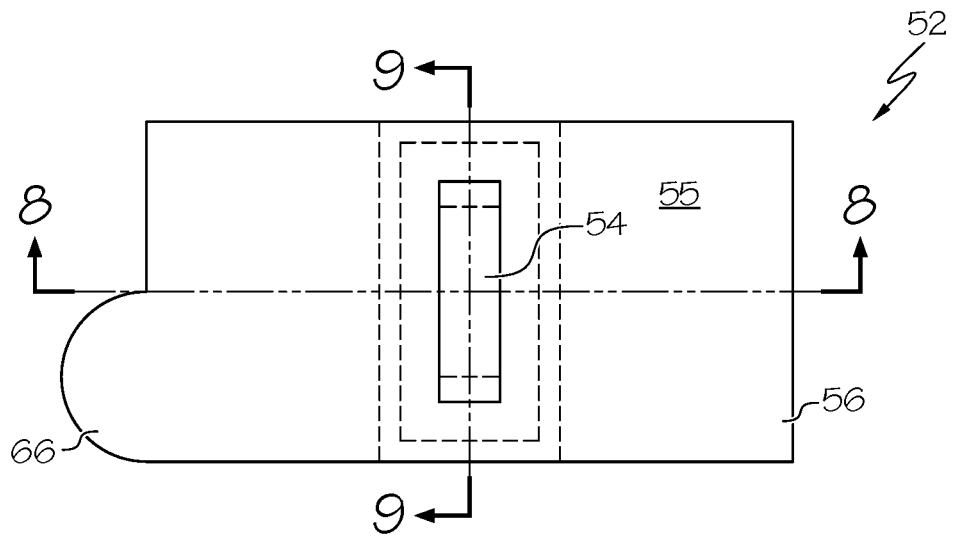
FIG. 7 is a top view of a second embodiment described herein.
Figure 8:
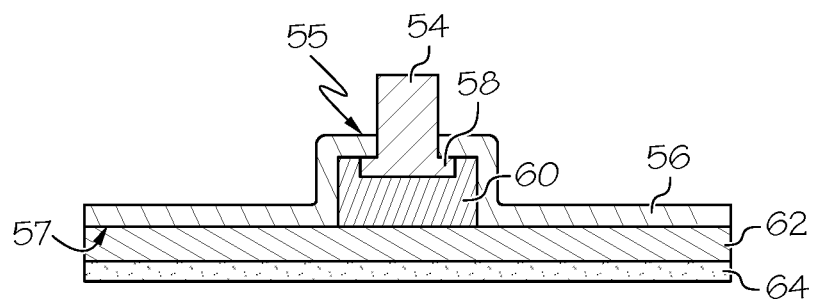
FIG. 8 is a front sectional view of the embodiment of FIG. 7 taken along lines 8-8.
Figure 9:
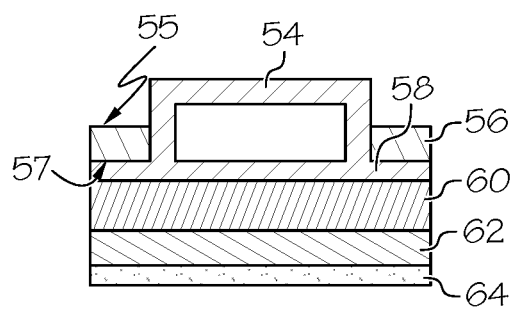
FIG. 9 is a side sectional view of the embodiment of FIG. 7 taken along lines 9-9.
Figure 10:
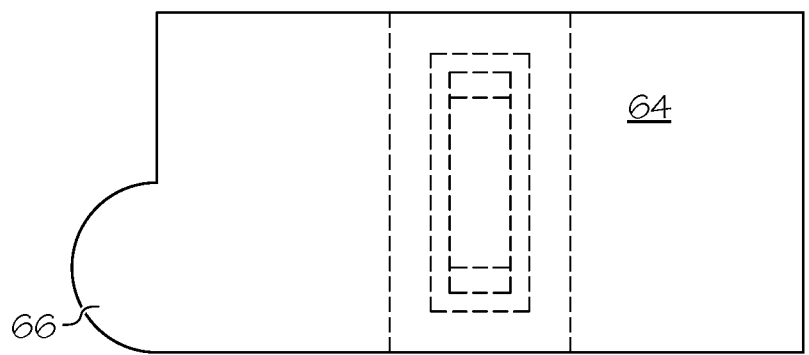
FIG. 10 is a bottom view of the embodiment of FIG. 7.

A second embodiment 50 is designed to work with fetal monitor belts having Velcro straps and is shown in FIGS. 7-12. The second embodiment 50 includes a pair of second embodiment devices 52A, B, shown in FIGS. 11 & 12. Turning now to FIG. 7, each device 52 includes a belt loop 54 fixed to the surface of a patch of fabric 56 having an upper fabric side 55 and a lower fabric side 57, as shown in FIG. 8. The belt loop 54 has a support member 58 located beneath the lower fabric side 57. A cushioning layer 60 is located to each side and below the support member 58 and adjacent to a portion of the lower fabric side 57. A layer of adhesive 62 extends below the cushioning layer 60 and the lower fabric side 57 not covered by the cushioning layer. A liner 64 covers the adhesive 62 until use. The liner 64 has a tab 66 extending outwardly from the profile of the fabric 56. The tab 66 is designed to be able to be easily grasped during use, which will be explained in detail below.

Figure 11:
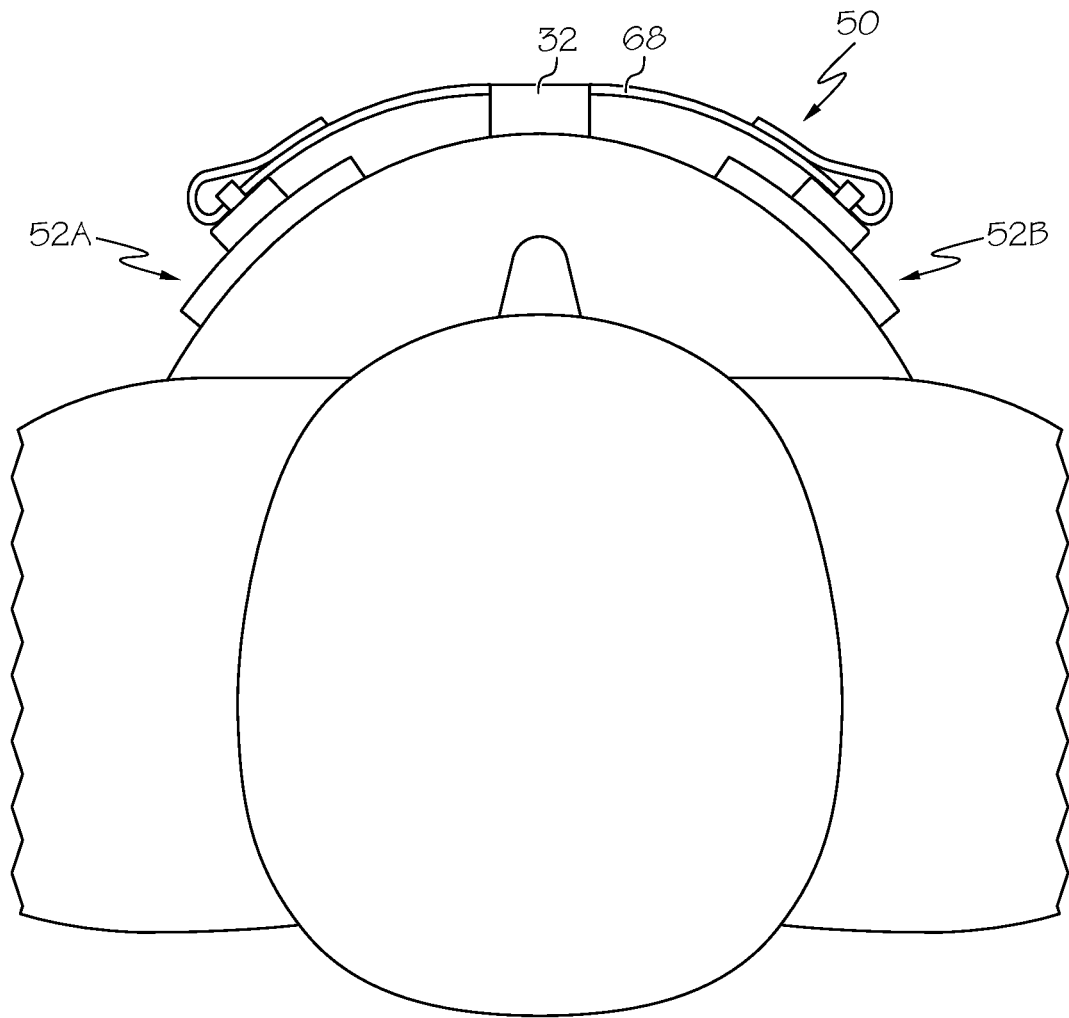
FIG. 11 is a front view of the second embodiment in use.
Figure 12:
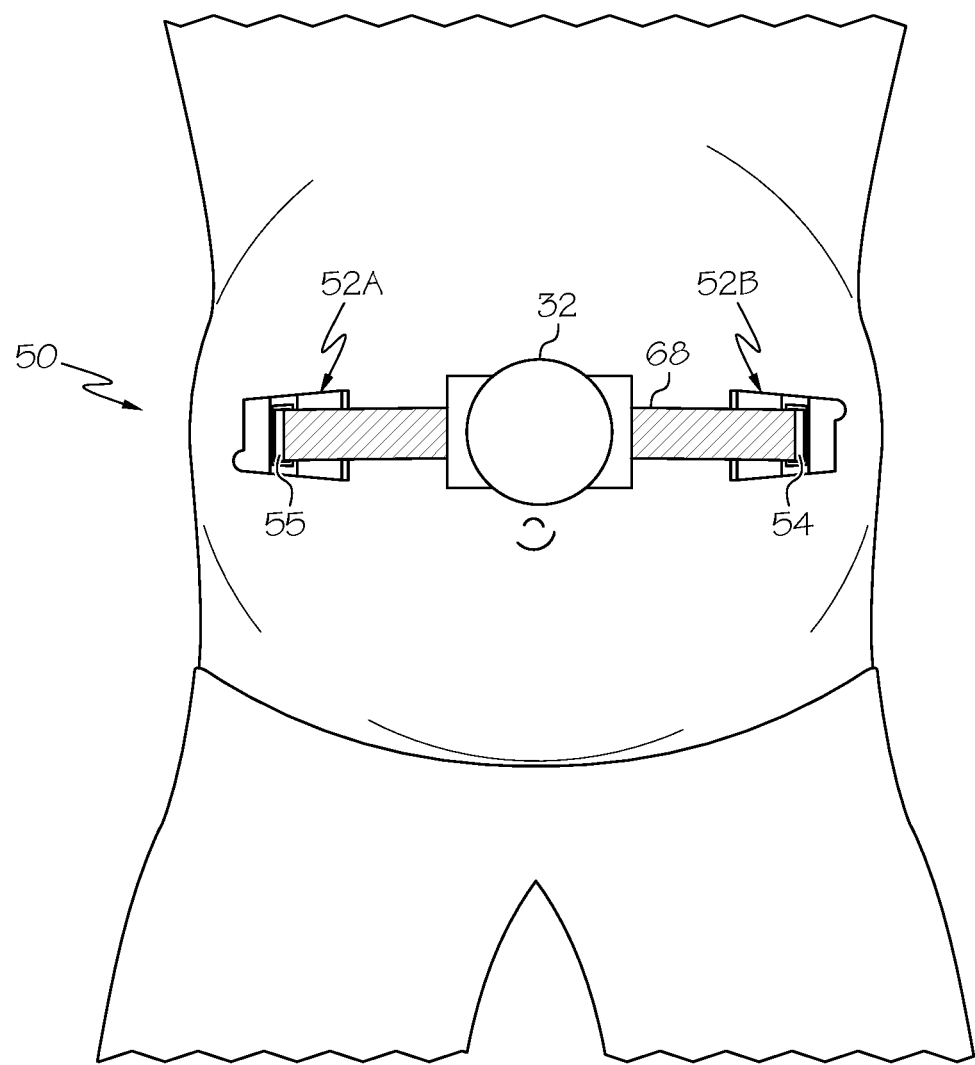
FIG. 12 is a top view of the embodiment of FIG. 11.

The second embodiment 50 works similarly to the first embodiment 10 in that a pair of the second embodiment devices 52A, B are used to anchor a medical transducer, typically a fetal heart rate transducer 32 in a fixed position. The second embodiment 50 is used when the particular brand of fetal heart rate transducer 32 has Velcro straps 68 fixed to or extending therefrom. These include the General Electric Corometric™ series. Once the position of the FHR transducer 32 is known, a first device 52A is positioned to one side of the FHR transducer 32 similarly as described above for the first embodiment device 10. Once the first device is positioned 52A against the skin of the patient, a second device 52B is positioned in an opposing direction with the transducer 32 to be located therebetween. After the second device 52B is fixed against the patient's skin, the Velcro strapping 68 is slipped through the belt loop 54 of the first second embodiment device 52A. The remaining length of the strapping 64 is folded back against the strapping and, due to the loop and hook nature of Velcro, it is secured against itself. The final positioning of the FHR transducer 32 and devices 52A and B is shown in FIGS. 11 and 12.

It should be noted that the second embodiment 50 shows the belt loop 54 located at the mid-section of the length of the second embodiment device 52. However, it is contemplated that the belt loop may be positioned closer to one end of the second embodiment device 52 to provide for a greater area of adhesion to hold the second embodiment device 52 in position when tensioned in use.

Figure 13:
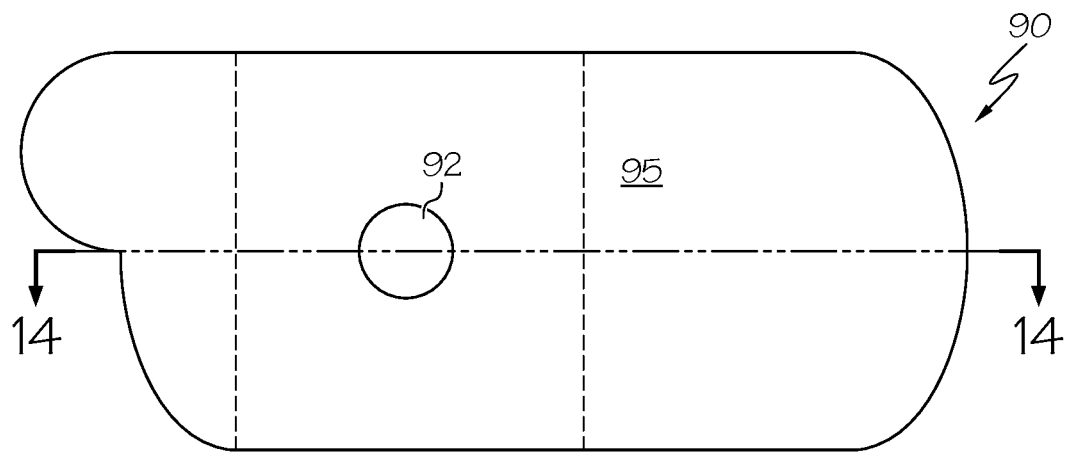
FIG. 13 is a top view of a third embodiment described herein.
Figure 14:
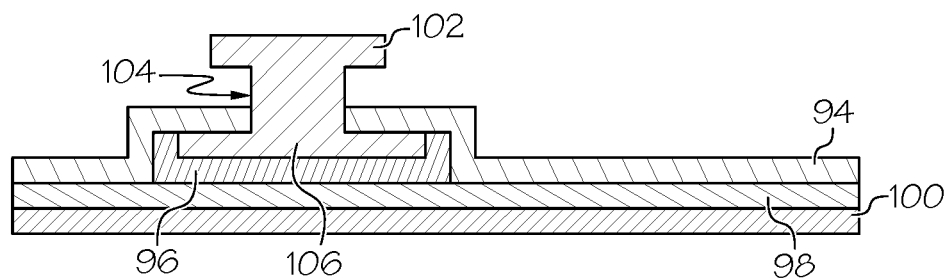
FIG. 14 is a front sectional view of the embodiment of FIG. 13 along lines 14-14.
Figure 15:
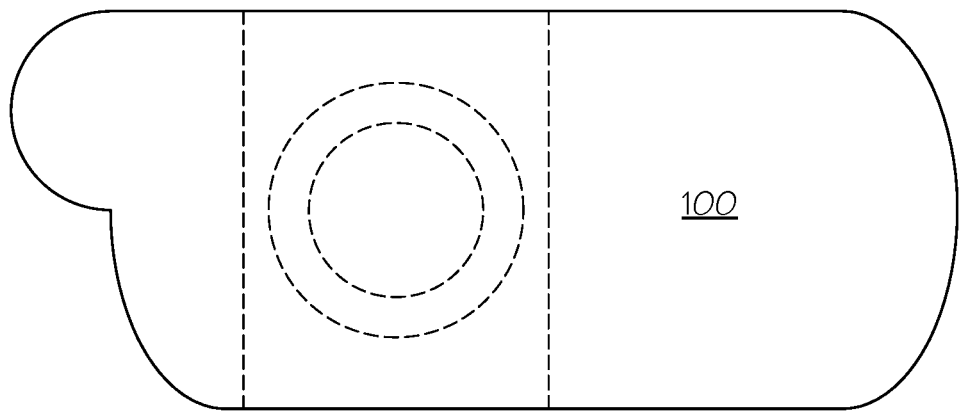
FIG. 15 is a bottom view of the embodiment of FIG. 13.

A third embodiment 90 is shown in FIGS. 13-17. The third embodiment 90 is similar to the first embodiment 10 except that the button 92 assembly of the third embodiment is located at a position off-center relative to the fabric layer 94, as shown in FIGS. 13-15. The third embodiment 90 is a device 91 having a button assembly 92, and fabric 94, cushion 96, adhesive 98 and liner 100 layers. The button assembly 92 of the third embodiment 90 includes a third embodiment button 102, a button stem 104 and a button base 106. The button assembly 92 is positioned so that the fabric layer 94 covers the upper surface of the button base 106. The cushion layer 96 covers the lower surface of the button base 106. The adhesive layer 98 covers the cushion layer and the lower surface of the fabric layer 94. The liner 100 covers the adhesive layer 98 until use.

The button assembly 92 of the third embodiment device 91 is mounted off center relative to the fabric layer. As can be seen in FIG. 13, the button assembly is closer to one end of the length of the fabric layer than the other end. The off-center positioning of the button assembly 92 on the fabric layer 94 allows a greater area of the adhesive layer 98 to be applied to the patient's skin on the side opposite from where the transducer is located. The greater adhesive area helps to anchor the device 91 against the tension force created by the strapping 38 which pulls on the device 91 in a direction towards the transducer 32.

Figure 16:
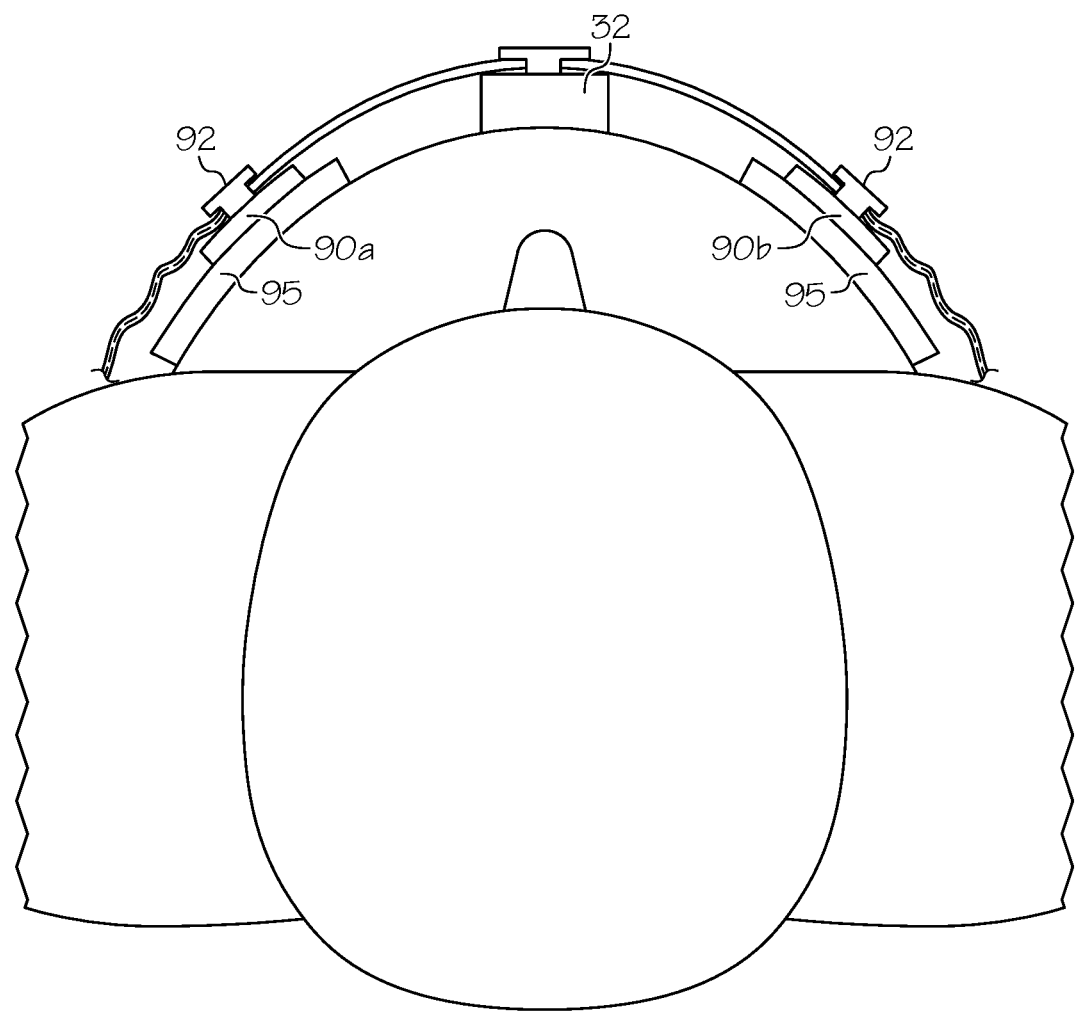
FIG. 16 is a front view of the embodiment of FIG. 13 in use.
Figure 17:
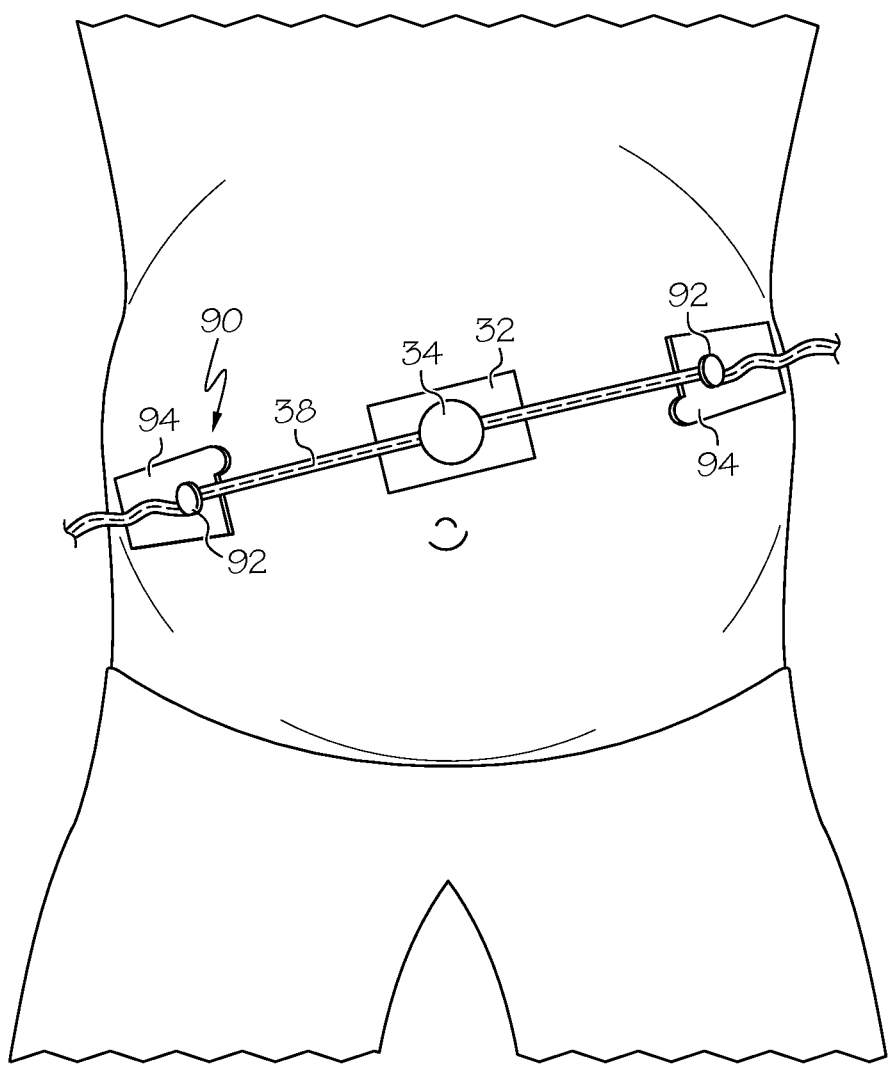
FIG. 17 is a top view of the embodiment of FIG. 16.

In use, once the position of the transducer 32 is set, the first, third embodiment device 91A is positioned by removing the liner 100 from the lower surface of the adhesive layer 98. The first third embodiment device 91A is positioned so that the button 102 is closer to the transducer 32 location. The second third embodiment device 91B is secured in the same fashion as described above but in a direction opposite from the location of the first third embodiment device 91A and on the opposed side of the transducer 32, as shown in FIGS. 16 and 17. This embodiment enables the devices 91A, B to withstand the tension imposed on each device by the strapping 38 while maintaining the position of the transducer 32.

Another component that may be used with either the first 10 or third 90 embodiments is a wedge attachment 70, as shown in FIGS. 18-22. As an example, the wedge attachment as described herein will be used with the third embodiment. However, the wedge attachment 70 is also able to be used with the first embodiment 10. The wedge attachment 70 is made of a rigid material that can be maintain its shape when used in conjunction with the first 10 or third 90 embodiments. The wedge attachment 70 is preferably made of a medical grade polymer for easy cleaning.

Figure 18:
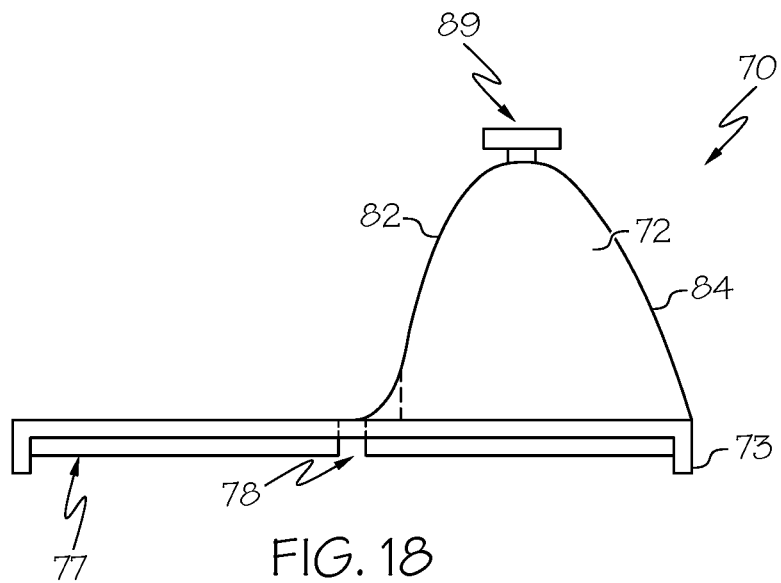
FIG. 18 is a front view of a wedge attachment.
Figure 19:
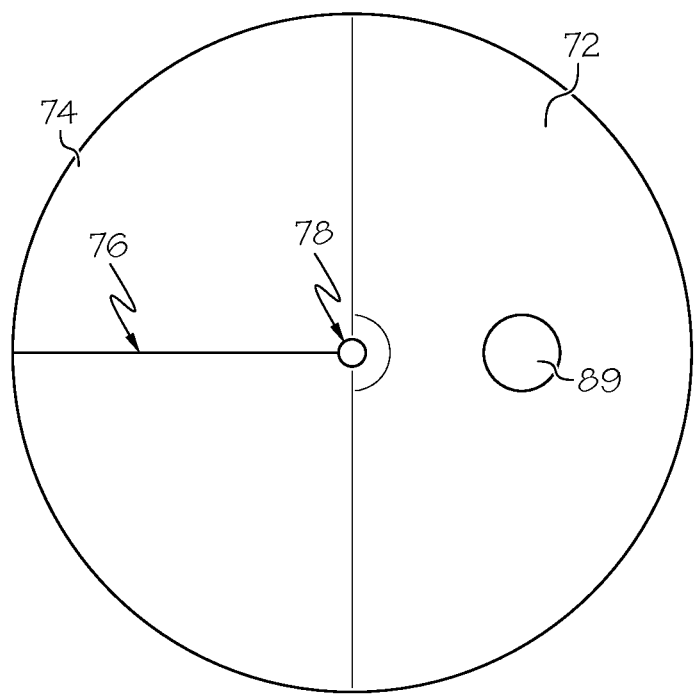
FIG. 19 is a top view of the wedge attachment of FIG. 18.
Figure 20:
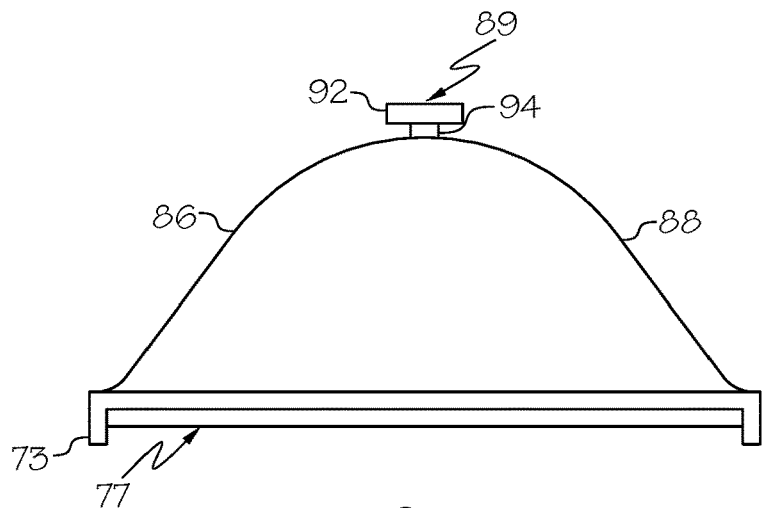
FIG. 20 is a side view of the wedge attachment of FIG. 18.
Figure 21:
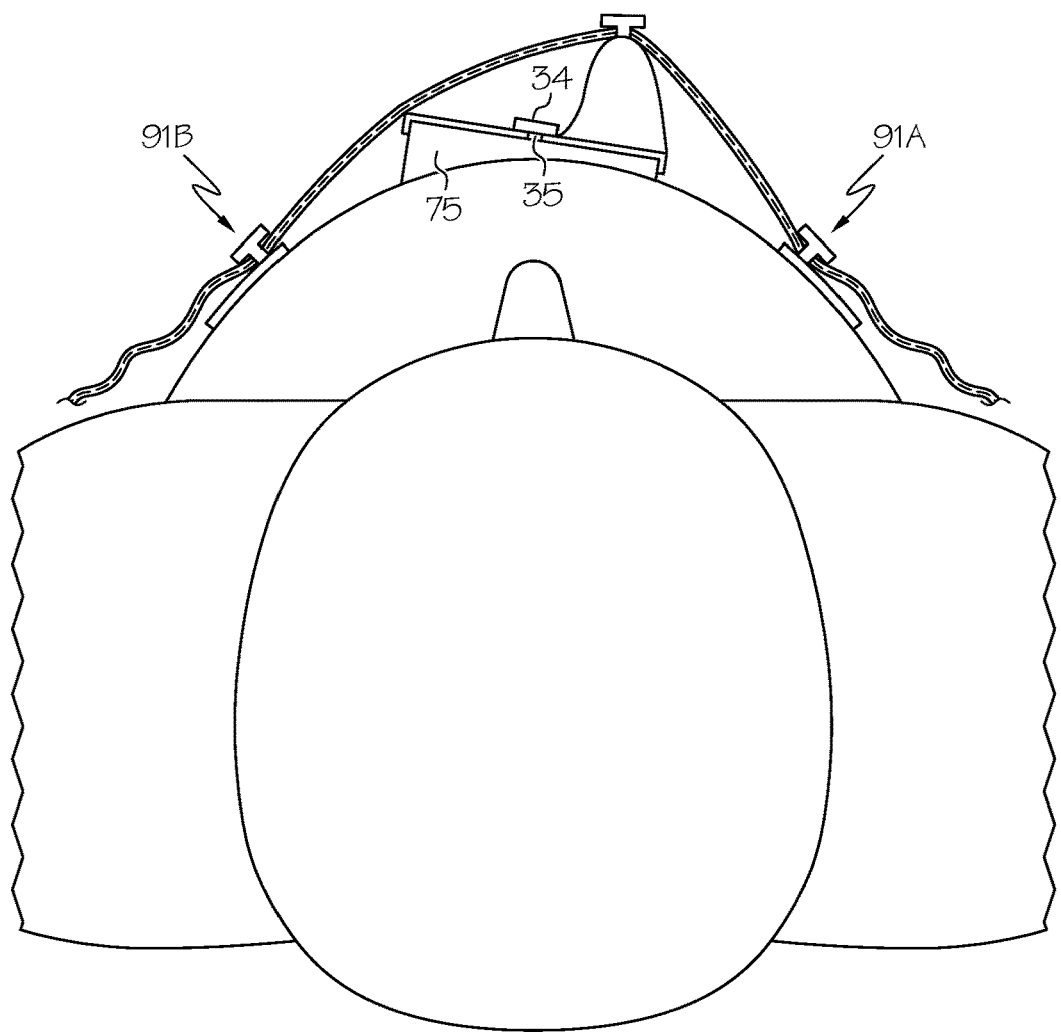
FIG. 21 is a front view of the embodiment of FIG. 18 in use.
Figure 22:
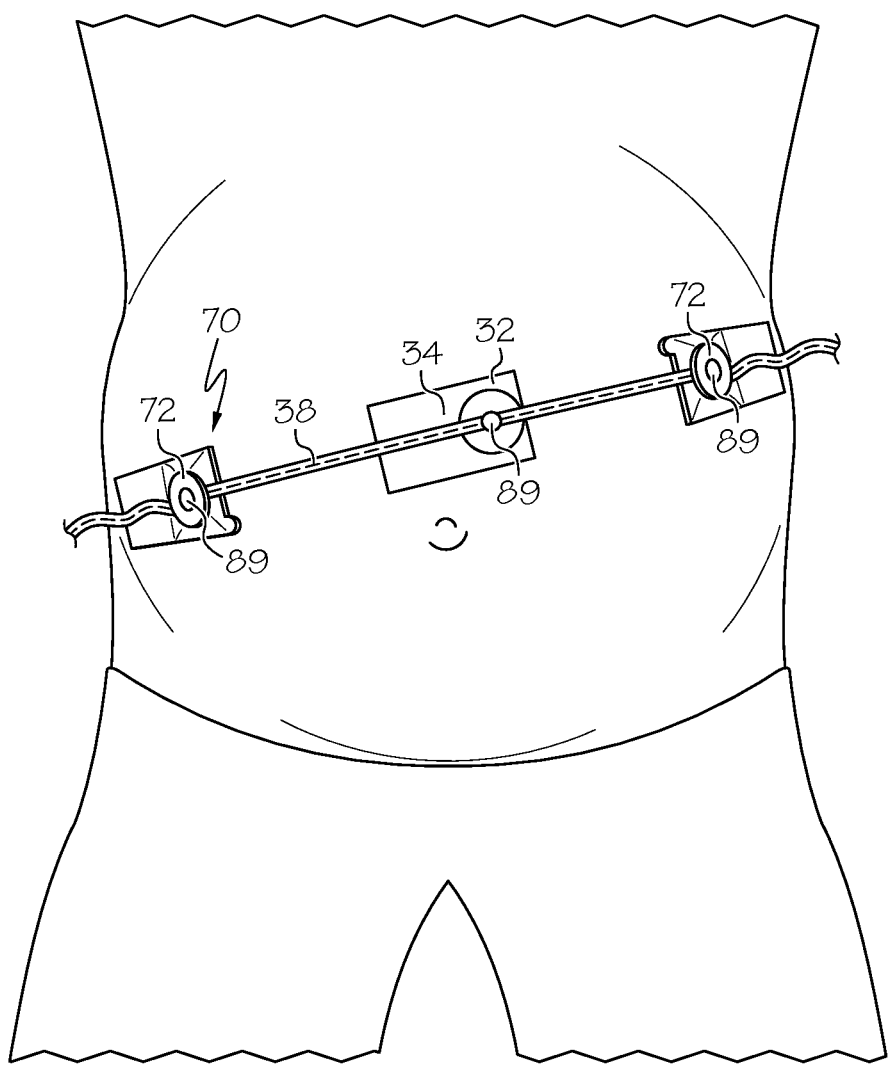
FIG. 22 is a top view of the embodiment of FIG. 21.

The wedge attachment 70 has a body 72 fixed to a circular platform 74, as shown in FIG. 19. The platform 74 has a radial slit 76 extending from the edge to the center of the platform. The center of the platform 74 has a small circular void 78. The void 78 is designed to be received by a standard FHR transducer, as will be described in more detail below. The platform 74 also has a lip 73 extending downwardly around the edge thereof, as shown in FIG. 18. The platform 74 further includes an undersurface 77 preferably made of a non-slip material such as rubber or a non-slip polymer.

FHR transducers are typically disc-shaped and have a standard size. Thus the wedge attachment 70 can be manufactured and scaled to be received by standard disc-shaped FHR transducers. The circular shape of the platform 74 is designed to rest on the upper surface of a standard fetal heart rate transducer 75. The circular void 78 is designed to receive the knob stem 35 located on a standard fetal heart rate transducer 75.

The wedge body 72 is located off center relative to the circular platform 74, as shown in detail in FIG. 18. The body 72 is sloped and has a substantially sinusoidal profile in both the front and side aspects, see also FIG. 20. Returning to FIG. 18, the body has front left 82 and front right 84 slopes, and side left 86 and side right 88 slopes, shown in FIG. 20. A wedge button 89 is fixed to the top of the body 72. The wedge button 89 has a disc shaped upper portion 92 fixed to a base 94 fixed to the wedge body 72, as shown in FIG. 19. The wedge button 89 is sized and shaped similarly to the FHR transducer knob 34.

To use, the wedge attachment 70 must first be positioned over the FHR transducer 75. To fit the wedge attachment over the FHR transducer 75, the radial slit 76 is pulled apart to enable the FHR transducer knob stem 35 to receive the slit 76 on either side thereof and then the stem 35 rests within the wedge void 78. In this position, the FHR transducer 75 rests beneath the wedge attachment 70 and the lip 73 of the platform 74 extends downwardly around the outer edge of the upper surface of the transducer to hold the transducer 75 in place. The non-slip material of the undersurface 77 grips the upper surface of the transducer 75 so that wedge attachment 70 and FHR transducer the two operate as one unit.

Once the wedge attachment 70 is fixed over the FHR transducer 75, the position of the FHR transducer is determined. This may involve moving the FHR transducer 75 and wedge attachment 70 around until the FHR signal is strong. Once the position is determined, the position of each of the devices 91A and B, of the third embodiment are determined. Once the position of each third embodiment device 91 is determined, the liner 20 is removed from the first third embodiment device 91A and placed against the skin of an expecting mother with the button 102 positioned closer to the FHR transducer 75. Subsequently the second third embodiment device 91B is positioned by removing the liner 20 and placing the embodiment on the skin at the desired location. It should be noted that the button 102 of the second third embodiment device 91 should be positioned closer to the desired location of the transducer 75.

Next, a slit 40 along the midpoint in a length of strapping 38 is received into the wedge button 89. A slit 40 at a first end of the strapping 38 subsequently receives the button 102 from the first third embodiment device 91A, and a slit at the other end of the strapping receives the button from the second third embodiment device 91B. The strapping tension may then be adjusted by changing the slit that is received into the button 102 on either third embodiment device 910 and also on the wedge button 89. The off-center aspect of the wedge attachment 70 causes an uneven distribution of the tension force created in the strapping 38. This results in an angling of the wedge attachment 70 which also results in an angling of the FHR transducer fixed thereunder. Thus, the wedge attachment 70 enables the FHR transducer 75 to maintain an angled position relative to the skin surface. This angled position is often extremely advantageous for obtaining and maintaining the FHR because the fetus may be in a position that is not easily measured when the FHT is placed flat against the mother's skin. The position and extent of the angled FHR transducer 75 can be adjusted by increasing or decreasing the tension in the strapping 38 and also by rotating the wedge attachment 70 so that the force is redistributed and thus the angle of the FHR transducer relative to the skin surface is changed.

It should also be noted that in this example and in other configurations, additional devices may be added to the configuration to further stabilize the position of the FHR. This is done by positioning the additional device, or devices and connecting them to the FHR transducer by means of the strapping 38. The strapping 38 is received into the device button and into the transducer knob 34 to provide further tension on the configuration and thus stabilize the position of the FHR transducer.

Figure 23:
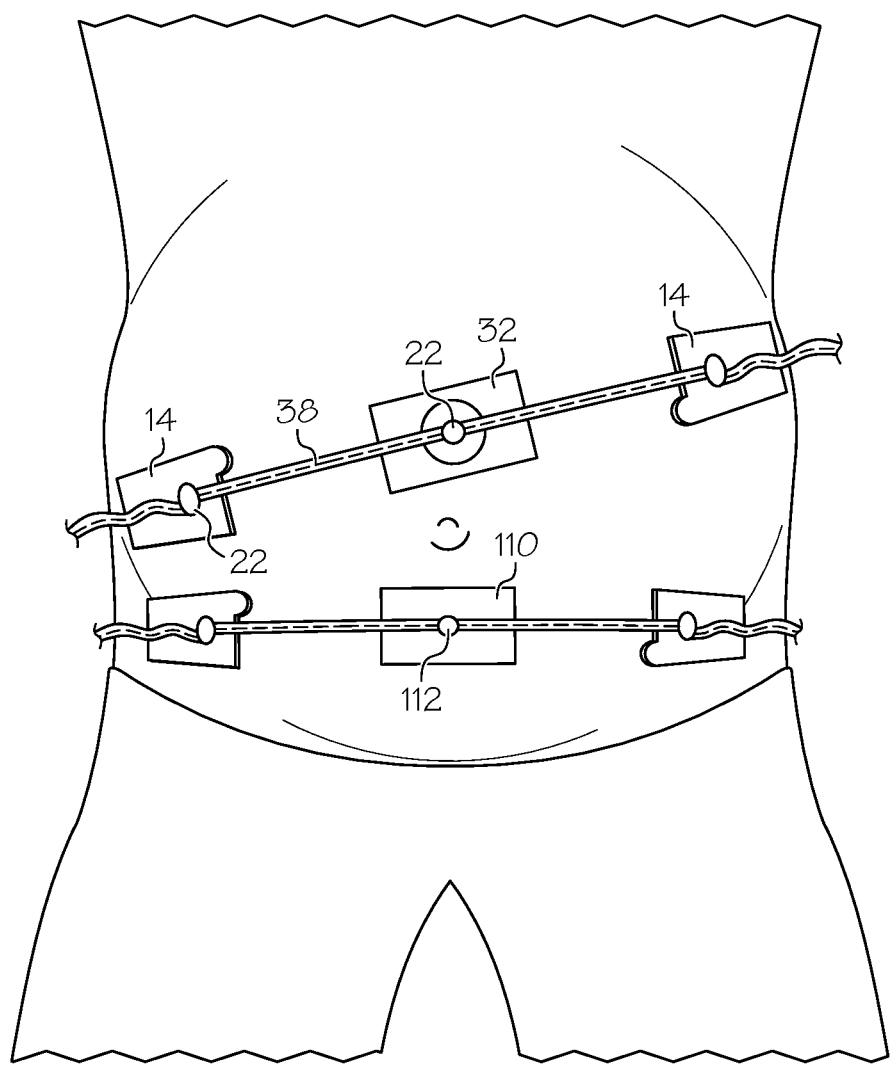
FIG. 23 is a top view of the embodiment of FIG. 22 in use with a contraction monitor.

One example of an arrangement involving the FHT and an additional device is shown in FIG. 23. The arrangement includes the addition of a compression monitor ("CM") 110. The compression monitor is similar to an FHT in that it is a transducer that monitors the labor contractions of the mother. The CM includes a button 112 to receive a slot 40 in the strapping 38. During labor and delivery, it is common practice to concurrently apply both a CM 110 and an FHT 32 to the skin surface of a mother, as shown in FIG. 23.

As discussed above, the plurality of devices connected by strapping help to create an infinite number of configurations for the positioning of the FHR transducer. The rotation of the wedge attachment 70 about the upper surface of the FHR transducer, or other device, helps to create an infinite number of positions of the FHR transducer, or other device, relative to the skin surface of the mother.

Between the device configurations and the wedge attachment rotation, medical personnel are able to customize a configuration for each patient based on the patient's anatomy and position as well as the fetal location and position. This system provides accurate and continuous FHR monitoring on an individualized basis and frees up medical personnel to attend to other, often more urgent matters. The system further provides a level of freedom to the mother to enable her to move freely within her bed or even stand and walk around while securing the FHR transducer in the desired position.

The invention claimed is:

1. An assembly for securely positioning a fetal heart transducer against the skin of an expectant mother, the assembly comprising:
   strapping having a length, the length having incremental openings thereon;
   first and second securing devices, each securing device comprising a body having a first surface and a second surface, the first surface having adhesive thereon, and a protuberance extending outwardly from the second surface in a direction opposed to the first surface, the protuberance to be received by one of the incremental openings in the strapping; and
   the fetal heart transducer having a first skin contacting transducer surface and a second transducer surface opposed to the first transducer surface; and
   a wedge attachment having a wedge base, a wedge body and a wedge button, the wedge base sized to be smaller than the second transducer surface, the wedge body having a sinusoidal profile in both front and side aspects, the wedge button being disc shaped and located at the top of the wedge body, the wedge button sized to be received into at least one incremental opening along the length of the strapping, whereby the first surface of the first securing device is secured to the skin surface of the expectant mother at a first location and the protuberance of the first securing device is received into a first incremental opening on the strapping, and the first surface of the second securing device is secured to the skin surface of a patient at a second location and the protuberance of the second securing device is received into a second incremental opening on the strapping, and the wedge base is positioned on the second transducer surface between the fetal heart transducer and the strapping, whereby when the strapping is pulled taut, the first skin contacting transducer surface is angled at least 10° from the horizon and against the mother's skin.

2. The assembly of claim 1 wherein the wedge attachment is comprised of an elastomeric foam.

3. The assembly of claim 1 wherein the strapping is comprised of medical grade fabric.

4. The assembly of claim 1 wherein the adhesive is medical grade.

5. The assembly of claim 1 wherein the assembly further comprises an additional device a to be received by at least one opening of the strapping along the length of the strapping between the first and second openings.

6. A method of anchoring a fetal heart transducer to the skin surface of an expectant mother comprising the steps of:
   providing a strip of elastic material having a length, and having incremental openings along the length thereof, the strip having first and second ends;
   providing first and second securing devices, each device comprising a body having a first surface and a second surface, the first surface having adhesive thereon, and a protuberance extending outwardly from the second surface in a direction opposed to the first surface, the protuberance to be received by one of the incremental openings along the length of the strip;
   providing a fetal heart transducer having a first skin contacting transducer surface and a second transducer surface opposed to the first skin contacting transducer surface;
   providing a wedge attachment having a wedge base, a wedge body and a wedge button, the wedge body having a sinusoidal profile in both front and side aspects, the wedge button being disc shaped and located at the top of the wedge body, the wedge button sized to be received into at least one of the incremental openings along the length of the strip,
   determining the desired position of the fetal heart transducer;
   positioning the first securing device at a first location adjacent to the desired position of the fetal heart transducer by placing the first surface of the first securing device against the skin surface of the expectant mother thereby affixing the first securing device in place;
   positioning the second securing device at a second location adjacent to the desired position of the fetal heart transducer and opposed to the position of the first securing device, the positioning occurring by placing the first surface of the second securing device against the skin surface of the expectant mother thereby affixing the first securing device in place;
   causing an incremental opening at the first end of the strip to be received into the protuberance of the first securing device;
   causing an incremental opening at the second end of the strip to be received into the protuberance of the second securing device;
   positioning the fetal heart transducer beneath the strip so that the first skin contacting transducer surface is adjacent to the skin surface of the expectant mother; and
   positioning the wedge base on the second transducer surface and causing the wedge button to be received into one of the incremental openings along the strip, whereby the first skin contacting transducer surface remains adjacent and angled at least 10° from the horizon and adjacent to the skin surface of the expectant mother.

7. The method of claim 6 wherein the wedge attachment is comprised of an elastomeric foam.

8. The method of claim 6 wherein the strip is comprised of medical grade fabric.

9. The method of claim 6 wherein the adhesive is medical grade.

10. The method of claim 6 wherein the fixation devices are circular in cross-section.

* * * * *